(12) United States Patent
Brunnett

(10) Patent No.: US 7,023,952 B2
(45) Date of Patent: Apr. 4, 2006

(54) MECHANICAL DAMPER FOR AIR PAD INSTABILITY

(75) Inventor: William C. Brunnett, Concord, OH (US)

(73) Assignee: Koninklijke Philips Electronics, Eindhoven (NL)

( * ) Notice: Subject to any disclaimer, the term of this patent is extended or adjusted under 35 U.S.C. 154(b) by 367 days.

(21) Appl. No.: 10/262,486

(22) Filed: Oct. 1, 2002

(65) Prior Publication Data

US 2004/0062356 A1    Apr. 1, 2004

(51) Int. Cl.
*A61B 6/03* (2006.01)
(52) U.S. Cl. ............................................. 378/15; 378/4
(58) Field of Classification Search .................... 378/4, 378/15, 193, 197
See application file for complete search history.

(56) References Cited

U.S. PATENT DOCUMENTS

| | | | | |
|---|---|---|---|---|
| 3,743,059 A | * | 7/1973 | Morse et al. ................ | 384/536 |
| 4,583,912 A | * | 4/1986 | Ball et al. ...................... | 74/574 |
| 5,473,657 A | * | 12/1995 | McKenna ....................... | 378/4 |
| 5,868,503 A | * | 2/1999 | Bade ........................... | 384/536 |
| 6,276,145 B1 | | 8/2001 | Sharpless et al. ............. | 62/51.1 |
| 6,404,845 B1 | | 6/2002 | Sharpless et al. ............. | 378/15 |

FOREIGN PATENT DOCUMENTS

| | | |
|---|---|---|
| EP | 1 095 620 | 5/2001 |
| EP | 1 095620 A1 | 5/2001 |
| JP | 05155263 A * | 6/1993 |
| JP | 5-269124 | 10/1993 |
| WO | WO 01/07899 | 2/2001 |
| WO | WO 02/24072 | 3/2002 |

* cited by examiner

*Primary Examiner*—Edward J. Glick
*Assistant Examiner*—Chih-Cheng Glen Kao

(57) ABSTRACT

In a diagnostic imaging apparatus, a stationary gantry (24) and a rotating gantry (22) are interfaced by a plurality of air bearing elements (40). Lower air bearing elements bear the weight of the rotating gantry (22) which induce air hammering phenomena at a characteristic vibration frequency. To counteract the air hammering, a damping assembly (44) is mounted to at least one lower bearing element (40). The damping assembly (44) includes a damping mass (46) and an elastomeric connector (48) that are tuned to a frequency near the air hammer frequency to absorb the vibrational energy and damp the air hammer vibrations.

18 Claims, 3 Drawing Sheets

MECHANICAL DAMPER FOR AIR PAD INSTABILITY

BACKGROUND OF THE INVENTION

The present invention relates to medical imaging arts. In particular, it relates to a rotating gantry such as those found in $3^{rd}$ and $4^{th}$ generation CT scanners, and will be described with particular reference thereto. However, the invention will also find application in conjunction with other systems, such as nuclear cameras that use rotating gantries, and is not limited to the aforementioned application.

Typically, $3^{rd}$ and $4^{th}$ generation CT scanners are equipped with mechanical ball or roller bearing systems. Because there is physical contact between the bearings and the rotating gantry, there is friction and wear that occurs over usage of the scanner. Additionally, functional speeds of the rotating gantry are limited by mechanical the bearings.

In an effort to overcome the limitations of mechanical bearing systems for such medical imagers, fluid bearing systems are being used. Some fluid bearing systems include porous bearing pads that fit snugly to bearing races of the rotating gantry. When the bearing system is charged, a micro-thin layer of fluid is ejected from the porous bearing pads between the pads and the bearing races. This provides a virtually frictionless support for the rotating gantry.

In such a system, the bearing pads that bear the weight of the rotating gantry typically exhibit a phenomenon called air hammering. Because of the shape of the bearing pad, and the stress exerted on the bearing due to the weight of the gantry, minor pressure inconsistencies of the bearing can result in rotational wobbling of the bearing pads. Air hammering can lead to premature wear of the bearing pads around the edges, where they frequently come into contact with the race, premature wear of the race for the same reason, and excess noise from the scanner.

In attempts to counteract the vibrational disturbances due to air hammering, previous systems have included conventional spring and damper means. A damper is attached to a rigid body, such as the stationary gantry. This damper is then attached to the bearing element. This is a cumbersome setup, requiring amounts of space that might not be available in a cramped gantry system. Additionally, such dampers are removed from the bearing elements if the bearing elements are removed from the stationary gantry.

The present invention contemplates an improved apparatus and method, which overcomes the aforementioned limitations and others.

SUMMARY OF THE INVENTION

According to one aspect of the present invention, a diagnostic imaging apparatus is provided. First and second gantries define an imaging region. A bearing system includes a plurality of bearing elements, at least one of which exhibits a mechanical disturbance. A mechanical damper is mounted with the at least one bearing element that dampens the mechanical vibrations.

According to another aspect of the present invention, a method of diagnostic scanning is provided. A gantry is rotated about a subject in an examination region. The rotating gantry is supported by a plurality of bearing elements, at least one of which tends to vibrate at a characteristic frequency. The vibrations of the bearing element are dampened.

According to another aspect of the present invention, a CT scanner is provided. A plurality of bearing pads are movably mounted to a stationary gantry for supporting a rotating gantry. A mass is mounted to at least one of the bearing elements by a resilient element. An x-ray source is mounted to one of the gantries. An array of detectors receives x-rays from the x-ray source. A reconstruction processor reconstructs outputs of the detector array into an electronic image representation.

One advantage of the present invention resides in reduced wear of component parts of a fluid bearing.

Another advantage resides in reduced noise of a fluid bearing system.

Another advantage resides in increased rotational potential of the rotating gantry.

Another advantage resides in a damper that does not require attachment to a fixed body.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

DETAILED DESCRIPTION OF THE PREFERRED EMBODIMENTS

Figure 1:
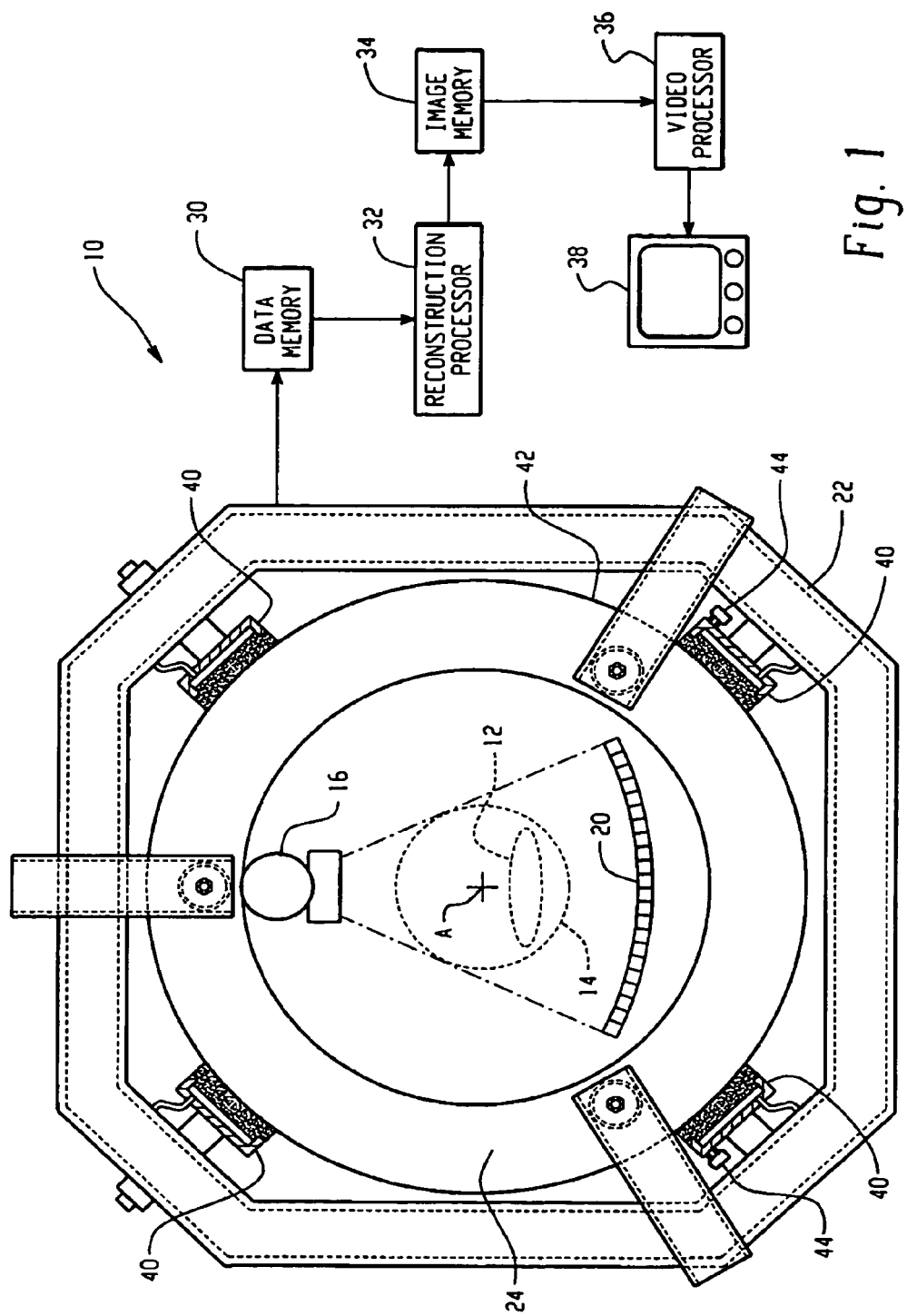
FIG. 1 is a diagrammatic illustration of a computed tomography scanner, in accordance with the present invention.

With reference to FIG. 1, a CT scanner 10 includes a subject couch 12 for moving a subject disposed thereon into and out of an imaging region 14. X-rays from an x-ray source 16 are shaped and collimated into a fan beam, pass through the imaging region 14 and are detected by a detector assembly 20 on the far side of the imaging region 14. In the illustrated $3^{rd}$ generation embodiment, the source 16 rotates concurrently with the detector assembly 20, always remaining 180° around the imaging region 14 from the detector assembly 20 as it rotates around an axis A. Alternately, a stationary ring of individual detectors on a stationary gantry 22 can replace the detector array 20, as in a $4^{th}$ generation CT scanner.

Intensities of detected x-rays are collected in a data memory 30 as a rotating gantry 24 rotates the x-ray source 16 about the subject. As the data is collected, a reconstruction processor 32 applies a convolution and backprojection algorithm, or other suitable reconstruction technique, to the collected data, forming an image representation. The image representation(s) are stored in an image memory 34. A video processor 36 withdraws selected portions of the image representations and formats them for viewing on a human readable monitor 38 such as a CRT monitor, active matrix monitor, LCD display, or the like.

The first, rotating gantry 24 is disposed within the second, stationary gantry 22. The x-ray source 16 and the detector array 20 are mounted on the rotating gantry 24. Radial air bearing elements 40 are attached to the stationary gantry 22 by ball joints and abut against a bearing race 42 of the rotating gantry 24. As discussed in the background, the weight of the rotating gantry 24 compresses the air bearing between the gantry 24 and the lower bearing elements 40 such that the phenomenon of air hammering tends to occur. Inertial dampers 44 are attached to the lower bearing elements 40 to dampen the movement of the air pads.

Figure 2:
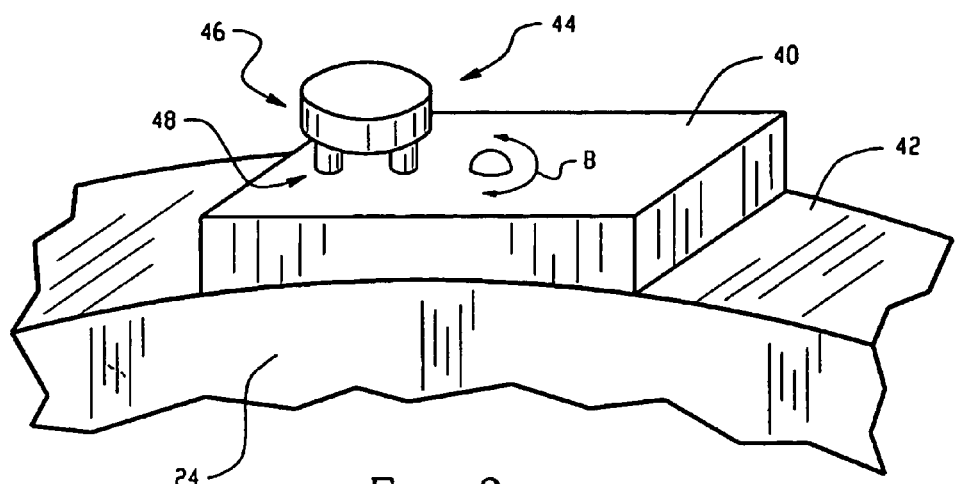
FIG. 2 is a perspective view of a lower air bearing element including an inertial damper, in accordance with the present invention.
Figure 3:
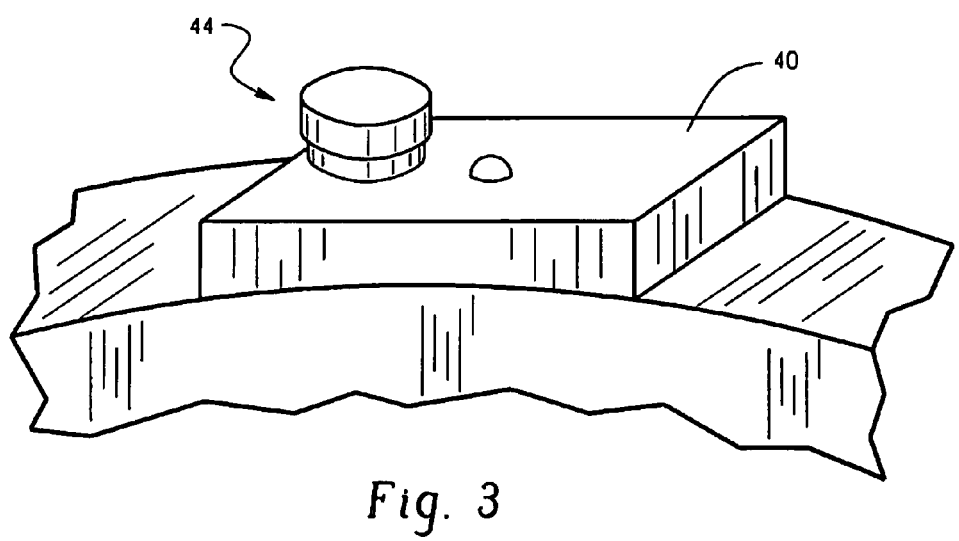
FIG. 3 is an alternate embodiment of the inertial damper of FIG. 2 with a single entity connector.

With reference to FIG. 2, the lower air bearing elements 40 exhibit air hammering, that is rotation indicated by the arrow B. The inertial damper 44 includes a damper mass 46 and a resilient, dampening connector 48. The mass 46 is sized proportionately to the bearing element 40 to have the greatest dampening effect at the resonant frequency of the hammering disturbance. Additionally, the farther away from the axis of rotation of the disturbance, (in this case the connection of the bearing element 40 to the stationary gantry 22) the more effective the damper will be. Preferably, the damper 44 is positioned at an extremity of the air bearing element 40, and can alternately be placed on a side of the bearing element 40 rather than the top as shown in FIGS. 1, 2, and 3. The mass 46 is connected to the bearing element 40 by the resilient connector 48. The connector 48 is made of high dampening elastomeric polymer. Suitable elastomers include, but are not limited to, Polyurethane and Urethane. The connector 48 taken in conjunction with the inertial mass 46 dampens the majority of the inherent air hammering.

The connector 48 acts as both a spring and a damper. The damping frequency of the damper mass 46 and the connector 48 is tuned to a frequency slightly less than the instability frequency of the bearing element 40. As the bearing element 40 starts to excite at its instability frequency, the bearing element 40 starts to excite the damper mass 46. The connector 48 absorbs some of that energy, thus reducing the motion of the bearing element 40. In the preferred embodiment, the connector includes a plurality of pins, each secured to the air bearing element 40 by a threaded connector. Alternately, and as shown in FIG. 3, the connector 48 can be a single elastomeric mass. It is to be understood that other connectors and adhesives are also contemplated.

Figure 4:
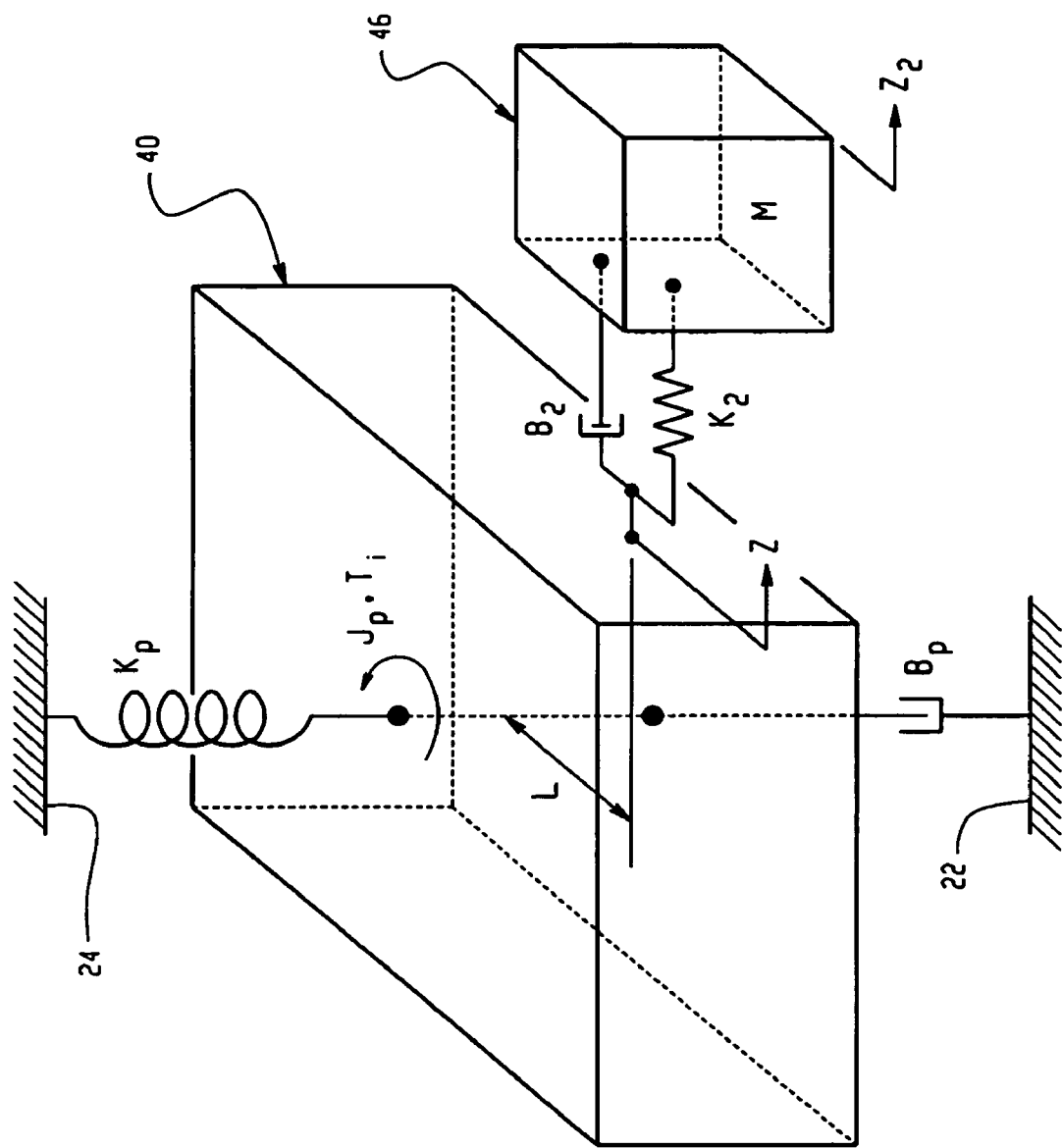
FIG. 4 is a schematic representation of the air bearing element of FIG. 2.

With reference to FIG. 4, the preferred embodiment can be seen in a mechanical schematic. The motion of the bearing element 40 and damper 44 system can be described by the following differential equations:

$$\ddot{z} = \frac{L}{J_p}\left[-\left(\frac{K_p}{L} + K_2 L\right)z - \left(\frac{B_p}{L} + B_2 L\right)\dot{z} + K_2 L z_2 + B_2 L \dot{z}_2 + T_1\right]$$

and $$\ddot{z}_2 = \frac{g_c}{M}[-K_2(z_2 - z) - B_2(\dot{z}_2 - \dot{z})]$$

where z is the position along one axis of the bearing element 40 and $z_2$ is the position along the same axis of the damper mass 46, L is the distance between a center of rotation of the bearing element 40 and an attachment point of the damper 44, $J_p$ is the rotational displacement of the bearing element 40, $K_p$ is the rotational spring constant of the air bearing itself, $K_2$ is the linear spring constant of the elastomeric connector 48, $B_p$ is the damping coefficient of an attachment of the bearing element 40 to the stationary gantry 22, $B_2$ is the damping coefficient of the connector 48, $T_i$ is the torque on the air bearing element 40, $g_c$ is the gravitational conversion constant and M is the mass of the damping mass 48.

From these equations, assuming that $K_p$, $J_p$, $T_i$, L, and $B_p$ are known or measured and fixed, appropriate values for $B_2$, $K_2$ and M can be determined.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic scanning apparatus comprising:
    a first, rotating gantry;
    a second, stationary gantry;
    an imaging region defined by a bore in the first gantry;
    an air bearing system including a plurality of bearing elements, at least one of the elements exhibiting mechanical disturbance;
    a mechanical damper mounted adjacent at least one bearing element to dampen the mechanical disturbance, the mechanical damper being not directly connected to the stationary gantry.

2. The diagnostic scanning apparatus as set forth in claim 1, wherein the mechanical disturbance is air hammering in a direction perpendicular to a direction of force applied by the bearing element to the rotating gantry.

3. The diagnostic scanning apparatus as set forth in claim 2, wherein the mechanical damper is attached to the bearing element at a point where the mechanical disturbance has the greatest amplitude.

4. The diagnostic scanning apparatus as set forth in claim 2, further including:
    a source of x-rays mounted to the rotating gantry for rotation therewith;
    a detector array for detecting x-rays originating from the source after they pass through the imaging region;
    a reconstruction processor for reconstructing the detected x-rays into an image representation.

5. The diagnostic scanning apparatus as set forth in claim 1 wherein the mechanical damper is tuned to a frequency near a characteristic vibration frequency of the mechanical disturbance.

6. A diagnostic scanning apparatus comprising:
    first and second gantries that define an imaging region;
    an air bearing system that connects the first and second gantries, the air bearing system including a plurality of bearing elements, at least one of the elements exhibiting mechanical disturbance;
    a damping mass for providing momentum opposite to momentum of the mechanical disturbance; and,
    an elastomeric connector that connects the damping mass to one of the air bearing elements and absorbs energy from the mechanical disturbance.

7. The diagnostic scanning apparatus as set forth in claim 6, wherein the elastomeric connector includes a plurality of rods connecting the bearing element to the damping mass.

8. The diagnostic scanning apparatus as set forth in claim 7, wherein the rods are each fastened to the bearing element with a threaded fastener.

9. The diagnostic scanning apparatus as set forth in claim 6, wherein the elastomeric connector is one of Polyurethane and Urethane.

10. The diagnostic scanning apparatus as set forth in claim 6, wherein the elastomeric connector and the damping mass are tuned to a frequency slightly less than a resonance frequency of the mechanical disturbance.

11. A method of diagnostic scanning comprising:
rotating a rotating gantry about a subject in an examination region;
supporting the rotating gantry on a plurality of bearing elements supported by a stationary gantry, at least one of which bearing elements tends to vibrate at a characteristic frequency;
mechanically damping the vibrating bearing element by mounting mass to the at least one bearing element with a resilient connector, the mass and resilient connector being not directly connected to the stationary gantry.

12. The method as set forth in claim 11, further including:
tuning the mass and the resilient connector to a damping frequency near the characteristic vibration frequency.

13. The method as set forth in claim 12, wherein the damping frequency is slightly less than the characteristic vibration frequency.

14. A method of diagnostic scanning comprising:
rotating a rotating gantry about a subject in an examination region;
supporting the rotating gantry on a plurality of air bearing elements which are supported by a stationary gantry, at least one of which bearing elements tends to vibrate at a characteristic frequency;
mechanically damping the vibrating bearing element with a damping element which is tuned to the characteristic frequency and not directly connected to the stationary gantry.

15. The method as set forth in claim 14, wherein the vibration of the air bearing element causes air hammering whose energy is absorbed by the mechanical damping to reduce the air hammering motion.

16. The method as set forth in claim 14, wherein the mechanical damping step includes:
absorbing energy with an elastomeric element and mass that are attached to the air bearing element.

17. The method as set forth in claim 14, further including:
emitting x-rays through the examination region;
detecting the x-rays after they pass through the examination region;
reconstructing the detected x-rays into an image representation.

18. A CT scanner comprising:
a stationary gantry;
a plurality of air bearing pads mounted to the stationary gantry;
a mass mounted to at least a lower one of the air bearing pads with a resilient element, the mass being not directly connected to the stationary gantry;
a rotating gantry having an annular race supported by the air bearing pads;
an x-ray source mounted to the rotating gantry;
an array of x-ray detectors mounted to one of the rotating and stationary gantries for receiving x-rays from the x-ray source;
a reconstruction processor connected with the detector array for reconstructing outputs of the detector array into an electronic image representation.

* * * * *